United States Patent [19]

Schalke et al.

[11] Patent Number: 4,542,240

[45] Date of Patent: Sep. 17, 1985

[54] PROCESS FOR THE PRODUCTION OF GUANIDINE HYDROCHLORIDE

[75] Inventors: Peter Schalke, Rodenbach; Langer Manfred, Karlstein; Klaus Huthmacher, Gelnhausen, all of Fed. Rep. of Germany

[73] Assignee: Degussa Aktiengesellschaft, Frankfurt am Main, Fed. Rep. of Germany

[21] Appl. No.: 237,728

[22] Filed: Feb. 24, 1981

[30] Foreign Application Priority Data

Feb. 28, 1980 [DE] Fed. Rep. of Germany ....... 3007530

[51] Int. Cl.$^4$ ........................................... C07C 128/00
[52] U.S. Cl. .................................................. 564/232
[58] Field of Search ........................ 564/232, 240, 241

[56] References Cited

U.S. PATENT DOCUMENTS

| | | | |
|---|---|---|---|
| 1,639,724 | 8/1927 | Cronshaw et al. | 564/232 |
| 1,886,087 | 11/1932 | Daudt | 564/232 |
| 2,194,075 | 3/1940 | Roblin, Jr. | 564/103 |
| 2,221,478 | 11/1940 | Hill et al. | 564/241 |

FOREIGN PATENT DOCUMENTS

| | | |
|---|---|---|
| 752750 | 9/1952 | Fed. Rep. of Germany . |
| 1593472 | 7/1970 | Fed. Rep. of Germany . |
| 1958095 | 5/1971 | Fed. Rep. of Germany . |
| 1267318 | 3/1972 | United Kingdom . |

OTHER PUBLICATIONS

Traube, J. *Berichte der Deutschen Chemischen Gesellschaft* (1885) at p. 462.

*Primary Examiner*—Natalie Trousof
*Assistant Examiner*—L. Hendriksen
*Attorney, Agent, or Firm*—Cushman, Darby & Cushman

[57] ABSTRACT

Guanidine hydrochloride is produced from cyanogen chloride in a new manner. The cyanogen chloride is reacted with ammonia in the absence of a solvent at a temperature of about 140° to 220° C. It is advantageous to add an ammonium salt at the beginning of the reaction and to use ammonia in at least stoichiometrical amounts.

27 Claims, No Drawings

PROCESS FOR THE PRODUCTION OF GUANIDINE HYDROCHLORIDE

BACKGROUND OF THE INVENTION

The invention is directed to a process for the production of guanidine hydrochloride.

It is known that in reacting dicyandiamide with ammonium chloride in the molten condition guanidine hydrochloride is formed (German Pat. No. 752750). Guanidine hydrochloride likewise is formed if dicyandiamide or cyanamide is heated with ammonium chloride at a temperature between 80° and 200° C. in a solvent consisting essentially of liquid ammonia (Hill U.S. Pat. No. 2,221,478). Also guanidine hydrochloride is produced by the reaction of cyanamide with ammonium chloride at a temperature of 120° to 170° C. in aqueous medium (German OS No. 1,593,472). A disadvantage of these processes is that the necessary starting materials, dicyandiamide or cyanamide must be obtained in several steps via calcium cyanamide from calcium carbide.

Besides it is known that in the action of cyanogen chloride on dimethylamine under pressure at a temperature of 130° to 180° C. in a water nonmiscible organic solvent 1,1,3,3-tetramethyl guanidine is formed (German Pat. No. 1,958,095). If it is attempted to react cyanogen chloride in a corresponding manner with ammonia to produce guanidine or guanidine hydrochloride there are not obtained satisfactory yields.

SUMMARY OF THE INVENTION

There has now been found a process for the production of guanidine hydrochloride which is characterized by reacting cyanogen chloride with ammonia in the absence of a solvent at a temperature of about 140° to 220° C. The process gives high yields of guanidine hydrochloride. The cyanogen chloride needed as starting material is obtained in a simple manner and with almost quantitative yield directly through catalytic reaction of chlorine with hydrogen cyanide, thus is substantially more easily accessible than the starting materials required for the known processes for the production of guanidine hydrochloride.

In carrying out the process of the invention it is generally suitable not to go substantially below the stoichiometric ratio of ammonia to cyanogen chloride, 2 moles of ammonia per mole of cyanogen chloride, namely to use not less than about 1.5 moles of ammonia per mole of cyanogen chloride. Although on the other hand, the ratio can be chosen as large as desired, i.e., the ammonia can be used in any excess desired, it is generally suitable not to employ more than about 10 moles of ammonia per mole of cyanogen chloride. Preferably the molar ratio of ammonia to cyanogen chloride is 2.0 to 5.0, especially 2.1 to 3.5.

According to the invention the reaction takes place in the absence of a solvent, especially an organic solvent, however, in many cases, for example to more readily draw off the heat occurring in the reaction, it can be advantageous to supply to the reaction medium inert gases such as nitrogen or air or argon. Ammonia can also serve as an inert gas, and in this case, it is employed in a large excess, suitably, however, not more than about 50 times the stoichiometrically required amount.

It can be advantageous to add an ammonium salt, especially ammonium chloride, at the beginning of the reaction. Although there can be used a wide range of amount of ammonium salt, generally it is advantageous that there be present about 0.01 to 0.10 mole, especially 0.02 to 0.05 mole, of ammonium salt per mole of cyanogen chloride. In place of the ammonium salt it should be understood that in case a corresponding amount of excess ammonia is available, then there can be added an acid, especially hydrogen chloride.

For the reaction there can be generally used temperatures of about 140° to 220° C., preferably from 160° to 200° C., especially from 175° to 200° C. In many cases, it can be advantageous to begin at a lower temperature, for example, at a temperature between −40° and 0° C., that is, the reactants are brought into contact with each other at this temperature and then heated to the actual reaction temperature of about 140° to 220° C.

The reaction can be carried out at any desired pressure, however, it is generally suitable, in order to use simple apparatus, to work at normal pressure (atmospheric pressure) or perhaps at slightly lowered or elevated pressure, up to about 5 bar.

There can be used both continuous and discontinuous methods of operating the process of the invention. In the continuous process it is advantageous to use a reactor in the form of a flow tube and to so supply the starting materials at its entrance that they are immediately intimately mixed with one another, further parts of the reaction mixture are recycled, for example using a loop reactor.

The guanidine hydrochloride obtained in the reaction can be freed from the impurities obtained in a given case in known manner, for example, it can be freed from ammonium chloride by adding a corresponding amount of guanidine carbonate.

Unless otherwise indicated, all parts and percentages are by weight.

The process can comprise, consist essentially of, or consist of the steps set forth with the recited materials.

DETAILED DESCRIPTION

EXAMPLE 1

There were led into a flask in uniform flow simultaneously gaseous cyanogen chloride and ammonia, namely in the course of one half hour 69.5 grams (1.13 moles) of cyanogen chloride and 64.6 grams (3.80 moles) of ammonia. Hereby the contents of the flask were held at −35° C. and the escape of ammonia prevented by means of a reflux condenser. Then the reaction mixture was heated, hereby the unreacted ammonia drawn off and subsequently the reaction mixture held for 2 hours with stirring at 180° C. The product, 97 grams, contained 92% of guanidine hydrochloride. The yield of guanidine hydrochloride, based on the cyanogen chloride employed consequently was 82%.

EXAMPLE 2

There were present in a flask 2.9 grams (0.05 mole) of ammonium chloride. Then in the course of one half hour there were simultaneously led into the flask 67.0 grams (1.09 mole) of gaseous cyanogen chloride and 56.1 grams (3.30 moles) of gaseous ammonia. Hereby the contents of the flask were constantly held at a temperature of 180° to 205° C. and the excess ammonia continuously driven off. Subsequently the reaction mixture was held at 180° C. for a further two hours under stirring. The product, 98 grams, contained 91% of guanidine hydrochloride. The yield of guanidine hydrochloride based on the cyanogen chloride employed was 86%.

EXAMPLE 3

In a flow tube having a length of 40 cm and 5 cm inside diameter, there were led in uniform, gaseous flow in the course of one hour 245 grams (4.0 mole) of cyanogen chloride and 148 grams (8.7 moles) of ammonia. The supply of the cyanogen chloride took place via a heated nozzle. The gases were mixed together at the entrance in the tube. The contents of the flow tube were held at 180° to 205° C. After leaving the flow tube, the reaction mixture was collected in a flask and stirred therein for 3 hours at 180° C. Hereby the unreacted ammonia was driven off. The product, 369 grams contained 94% of guanidine hydrochloride and 2% of ammonium chloride. The yield of guanidine hydrochloride, based on the cyanogen chloride employed, was 91%.

EXAMPLE 4

There were nozzled into a flow tube hourly in uniform flow, 22 grams (0.6 mole) of hydrogen chloride, 753 grams (12 moles) of cyanogen chloride and 238 grams (14 moles) of ammonia. Inside the flow tube the temperature was held at 190° C. The reaction mixture left the flow tube after an average residence time of 30 minutes. The unreacted ammonia was separated off and then the reaction mixture was held for a further 3 hours in a second flow tube at 190° C. After leaving the flow tube and cooling the reaction mixture solidified in crystalline form. It contained 96% guanidine hydrochloride and 3% ammonium chloride. There were recovered hourly 1196 grams, corresponding to a yield of guanidine hydrochloride at 98% based on the cyanogen chloride employed.

What is claimed is:

1. A process for producing guanidine hydrochloride comprising reacting cyanogen chloride with ammonia in the absence of a solvent at a temperature of 140° to 220° C.

2. A process according to claim 1 including the step of recovering the guanidine hydrochloride.

3. A process according to claim 1 wherein the materials employed consist essentially of (a) cyanogen chloride and ammonia, (b) cyanogen chloride, ammonia, and ammonium salt, or (c) cyanogen chloride, ammonia in excess of that required to react with the cyanogen chloride and an acid which can form an ammonium salt with the excess ammonia.

4. A process according to claim 3 wherein the materials employed consist of those set forth.

5. A process according to claim 3 wherein the temperature is 160° to 200° C.

6. A process according to claim 4 wherein there are employed 2.0 to 5.0 moles of ammonia per mole of cyanogen chloride.

7. A process according to claim 6 wherein there are employed 2.1 to 3.5 moles of ammonia per mole of cyanogen chloride.

8. A process according to claim 7 wherein the temperature is 160° to 200° C.

9. A process according to claim 3 wherein the materials employed consist essentially of cyanogen chloride and ammonia.

10. A process according to claim 3 wherein the materials employed consist essentially of cyanogen chloride, ammonia and an ammonium salt.

11. A process according to claim 10 wherein there are employed 0.01 to 0.10 moles of ammonium salt per mole of cyanogen chloride.

12. A process according to claim 11 wherein there are employed 2.0 to 5.0 moles of ammonia per mole of cyanogen chloride.

13. A process according to claim 12 wherein there are employed 2.1 to 3.5 moles of ammonia and 0.02 to 0.05 moles of ammonium salt per mole of cyanogen chloride.

14. A process according to claim 13 wherein the ammonium salt is ammonium chloride.

15. A process according to claim 12 wherein the ammonium salt is ammonium chloride.

16. A process according to claim 11 wherein the ammonium salt is ammonium chloride.

17. A process according to claim 10 wherein the ammonium salt is ammonium chloride.

18. A process according to claim 3 wherein the materials employed consist essentially of cyanogen chloride, ammonia in excess of that required to react with the cyanogen chloride and an acid which can form an ammonium salt with excess ammonia.

19. A process according to claim 18 wherein the ammonia is used in an amount of 2.1 to 50 mole per mole of cyanogen chloride.

20. A process according to claim 19 wherein the acid is hydrogen chloride.

21. A process according to claim 20 wherein there are employed 14 moles of ammonia and 0.6 mole of hydrogen chloride per 12 moles of cyanogen chloride.

22. A process according to claim 18 wherein the acid is hydrogen chloride.

23. A process according to claim 3 wherein the ammonia and cyanogen chloride are mixed together at a temperature of −40° to 0° C. prior to being heated to the reaction temperature.

24. A process according to claim 1, wherein the temperature is 160° to 220° C.

25. A process according to claim 1, wherein the temperature is 180° to 205° C.

26. A process according to claim 1, wherein the temperature is 190° C.

27. A process according to claim 1, wherein the temperature is 175° to 200° C.

* * * * *